United States Patent [19]
Forsgren et al.

[11] Patent Number: 5,718,909
[45] Date of Patent: Feb. 17, 1998

[54] SHEET CONTAINING CARBOHYDRATE DERIVATIVE FOR REMOVAL OF E. COLI

[75] Inventors: Arne Forsgren, Ealsterbo; Arne Lundblad, Uppsala, both of Sweden

[73] Assignee: Medscand AB, Malmo, Sweden

[21] Appl. No.: 528,543

[22] Filed: Sep. 15, 1995

Related U.S. Application Data

[63] Continuation-in-part of Ser. No. 107,678, filed as PCT/SE92/00093, Feb. 17, 1992, abandoned.

[30] Foreign Application Priority Data

Feb. 18, 1991 [SE] Sweden ............... 9100480

[51] Int. Cl.$^6$ ............... A01N 25/34; A01N 43/16
[52] U.S. Cl. ............... 424/402; 424/404; 424/405; 424/443; 424/78.17; 424/78.08; 424/78.18; 424/78.31; 424/78.32; 424/78.37; 424/78.38
[58] Field of Search ............... 424/402, 404, 424/78.02, 78.07, 78.17, 78.18, 405, 443

[56] References Cited

U.S. PATENT DOCUMENTS

| | | | |
|---|---|---|---|
| 4,828,984 | 5/1989 | Schwartz | 435/7 |
| 4,837,079 | 6/1989 | Quantrille et al. | 428/288 |
| 4,849,358 | 7/1989 | Chazano | 435/252 |
| 4,898,817 | 2/1990 | Yamazaki et al. | 435/49 |
| 4,939,123 | 7/1990 | Neeser et al. | 514/8 |

FOREIGN PATENT DOCUMENTS

| | | |
|---|---|---|
| 0 126 043 | 11/1984 | European Pat. Off. . |
| 0021 728 | 5/1987 | European Pat. Off. . |
| 3 408 653 | 9/1984 | Germany . |
| 463314 | 11/1990 | Sweden . |
| WO87/01400 | 3/1987 | WIPO . |
| WO89/05093 | 6/1989 | WIPO . |

OTHER PUBLICATIONS

Eshdat et al., "Isolation of a Mannose–Specific Lectin from Escherichia Coli and its Role in the Adherence of the Bacteria to Epithelial Cells", *Chemical Abstracts*, 90, Abs. No. 90:119508v, 470 (Apr. 1979).

Aronson et al., "Prevention of Colonization of the Urinary Tract of Mice with Escherichia Coli by Blocking of Bacterial Adherence with Methyl Alpha–D–Mannopyranoside", *Chemical Abstracts*, 91, Abstract No. 91:332k, 36.

Toyota et al., "Anti–Bacterial Defense Mechanism of the Urinary Bladder: Role of Mannose in Urine", *Chemical Abstracts*, 112, Abs. No. 112:176889s, 578 (May 1990).

Grant and Hackh's Chemical Dictionary, McGraw Hill Book Co. (1987), pp. 176–177.

Chernyak et al., "A New Type of Carbohydrate–Containing Synthetic Antigen: Synthesis of Carbohydrate–Containing Polyacrylamide Copolymers Having the Specificity of 09:3 and 0:4 Factors of Salmonella", *Carbohydrate Research*, 128:269–282 (1984).

Chernyak et al., "Two Synthetic Antigens Related to Streptococcus pneumoniae Type 3 Capsular Polysaccharide", *Carbohydrate Research*, 141:199–212 (1985).

Horejski et al., "O–Glycosyl Polyacrylamide Gels for Affinity Chromatography of Phytohemagglutinins", *Biochmica et Biophysica Acta*, 297:346–351 (1973).

Kosma et al., "Artificial Antigens. Synthesis of Polyacrylamide Co–Polymers Containing 3–Deoxy–D–manno–2–Octulo–pyransoylonic Acid (KDO) Residues", *Carbohydrate Research*, 167:39–54 (1987).

Kosma et al., "Synthesis of Polyacrylamide Copolymers Containing α–linked o–(3–Deoxy–D–manno–2–Octulopyranosylonic Acid) (KDO) Residues", *Carbohydrate Research*, 180:19–28 (1988).

Lee et al., "A Simple Method for the Preparation of Polyacrylamide Gels Containing Thioglycoside Ligands", *Analytical Biochemistry*, 95:260–269 (1979).

Roy et al., "N–Acetylneuroaminic Acid: Neoglycoproteins and Pseudopolysaccharides", *J. Carbohydrate Chemistry*, 6(1):161–165 (1987).

Roy et al., "Synthesis of Copolymer Antigens Containing 2–Acetamido–2–Deoxy–α–or β–D–Glucopyranosides", *Glycoconjugate J.*, 5:203–206 (1988).

V. Horejsi et al., "XXXV. Water–Soluble 0–Glycosyl Polyacrylamide Derivatives for Specific Precipitation of Lectins", Stuides on Lctins, *Biochimica et Biophyisica Acta* 538:293–298 (1978).

*Primary Examiner*—Jeffrey C. Mullis
*Attorney, Agent, or Firm*—Merchant, Gould, Smith, Edell, Welter & Schmidt, P.A.

[57] ABSTRACT

A sheet of nonwoven material which can be used as cleansing product in the form of a wet tissue for effective removal of bacteria, especially type 1 piliated *E. coli*, when wiping for example the hands, in connection with personal hygiene, or the like, wherein a carbohydrate derivative is incorporated in the sheet and by interaction with bacteria an effective removal of the bacteria from the cleaning site is achieved by the bacteria being bound to the carbohydrate derivative.

41 Claims, 11 Drawing Sheets

FIG.7B

SHEET CONTAINING CARBOHYDRATE DERIVATIVE FOR REMOVAL OF E. COLI

This application is a continuation in part of U.S. Ser. No. 08/107,678, filed as PCT/SE92/00093, Feb. 17, 1992, abandoned.

Swedish priority document No. 9100480-4 is hereby incorporated by reference thereto. Priority from this application, filed Feb. 17, 1992, is claimed.

The present invention refers to a new sheet of nonwoven material which can be used as a cleansing product in the form of a wet tissue for effective removal of bacteria, especially type 1 piliated *E. coli*, when wiping for example the hands, in connection with personal hygiene, or the like.

Urinary tract infections (UTI) rank first among the bacterial diseases of adults that come to attention of the physicians. The majority of patients are women. As many as 20% of all women have an episode of UTI by the age of 30. It is estimated that there are 3 million office visits for this complaint each year in the United States only. Recurrent episodes of urinary tract infections afflict about one of ten women at some time in their lives.

All parts of the urinary tract may be affected but the most common UTI are infections of the bladder (cystitis) and the pelvis or the kidney (pyelonephritis). UTI may also result in bacteriemia (sepsis). There are also many patients who persistently excrete large numbers of bacteria in the urine but are asymptomatic.

The majority (>90%) of bacteria causing UTI belongs to the family Enterobacteriacae (*E. coli*, Klebsiella, Enterobacter,Proteus). These bacteria are normal inhabitants of the intestine. There are different steps in the pathogenesis of urinary tract infection. The first important step is establishment of the faecal bacterial flora outside anus in the vaginal vestibule and the periurethral areas.

The much greater prevalence of UTI among women than men has been attributed to the fact that invading organisms make a shorter trip up the female urethra to reach the bladder. Sexual intercourse contributes to UTI, perhaps by "massaging" bacteria upward to the bladder, hence the term "honeymoon cystitis". The use of contraceptive diafragmas also seem to predispose to UTI. Women who are particularly prone to recurrent UTI have been found to possess a greater than normal density of receptors for bacteria on their cells. In other words, their epithelial cells are particularly "sticky" for bacteria. Women prone to UTI has also been shown by a high number of investigators to be colonized with faecal bacteria outside anus in the periurethral area.

Some bacterial factors facilitate colonization of bacteria in the genital tract and also infection. These factors are adhesions (pili, fimbriae) which are small threadlike organ cells surrounding the bacteria. During the last decade a vast amount of research has been made to understand the role of pili in UTI. There are two major classes of pili: p-pili and type 1 pili.

P-pili have been most studied due to the fact that P-pili have been found more frequently on the surface of bacteria causing more serious UTI:s (pyelonephritis) than on bacteria causing less serious UTI (cystitis). P-pili have been shown to cause adhesion of the bacteria to urinary bladder cells and thus have been thought to be responsible for persistence of bacteria in the urinary tract. It has also been shown that P-pili bind the bacteria to a disacharide unit on the surface of the urinary tract cells. This disaccharide contains galactose. It has been demonstrated that adhesion to urinary cells of bacteria with P-pili on their surface can be inhibited by a derivative of galactose. Thus, a vast amount of research has been devoted to research with the aim to use a derivative of galactose for treatment and prophylaxis of UTI. However, one of the problems has been that although a majority of *E. coli* bacteria causing pyelonephritis have P-pili on their surface, only half of *E. coli* bacteria causing cystis have this type of pili on their surface. Thus, today inhibition of P-pili is seeemingly not a useful method to prevent UTI.

The other type of pili mentioned above, type 1 pili, rather seems to be a major target for prophylaxis of UTI. Essentially all bacteria belonging to the family Enterobacteriaceae have the capacity to produce type 1 pili on their surface. That is *E. coli*, Klebsiella, Enterobacteriaceae and Proteus which are the cause of more than 90% of all UTI:s. The proposed main function of type 1 pili is to promote colonization of the large intestine Which is the natural ecological niche for Enterobacteriacae including *E. coli*. Receptors for type 1 pili have been demonstrated on buccal, intestinal, vaginal and urinary tract cells. These receptors for type 1 pili have been shown to contain mannose. Adherence to these cells of Enterobacteriacae including *E. coli* mediated by type 1 pili is blocked by D-mannose and some derivatives of this monosaccharide. Thus, a derivative of D-mannose could be used for effective prophylaxis of UTI.

However, the greatest challenge to-day is not treatment of the initial UTI-infection but the problem of recurrence. The acute infection usually can be treated successfully with antibiotics. On the other hand, the recurrent infections can not be treated or prohibited by antibiotics. Antibiotics rather increase colonization of the genital tract with antibiotic resistant UTI-causing bacteria.

Women with recurrent infections are significantly more often carriers of *E. coli* and other enterobacteria in the periurethral tract in comparison with normal controls. As mentioned above this is a major factor contributing to UTI in these women. Thus, the large group of women with recurrent UTI is informed by their physicians of rather nonspecific methods for prophylaxis of recurrent UTI like the importance of micturation hygiene (complete bladder emptying, postcoital bladder emptying), generous fluid intake particularly in elderly people, avoidance of pessaries and spermicides. Oestrogen substitution therapy should be recommended for women with recurrent cystitis after menopause. Postcoital short-term antibiotic treatment is effective in some patients. A good continuity in patient-doctor relationship is recommended for optimal management of this patient group. Nowadays most authorities in this field strongly recommended against long-term antibiotics in the prophylaxis of recurrent UTI:s.

As colonization with faecal bacteria outside anus in the vaginal vestibule and the periurethral area is a major factor contributing to UTI a wet tissue with D-mannose could be used for improved genital hygiene to selectively remove these UTI-causing bacteria. Today no other single recommendation can be given by physicians to reach this goal. The wet tissues could be used as a supplement to non-specific methods. Thereby the normal bacterial flora not causing UTI would not be influenced but *E. coli* and other Enterobacteriacae which might cause UTI can selectively be removed. The main target group could be women with recurrent infections.

A variety of products are known intended for wiping, cleansing etc., which either can be of the dry type, as for example facial tissues of different kinds, or of the wet type, so called wet wipes. The latter are supplied enclosed in a sealed envelope in order to prevent premature evaporation. All these known products are well suited for the intended purpose but fail in efficiency regarding the effective removal of bacteria from the site concerned. This applies especially to *E. coli* bacteria, when type 1 pillared.

The binding to the sheet can take place in an arbitrary way and can consist of a non-specific adhesion to the matrix of the cleansing product. Such adhesion can be achieved by simply dipping the sheet in a solution containing the active component which is sucked up into the material and after drying of the material remains there. When a substance binding to a pathogenic microorganism is incorporated into a sheet, such as a wet tissue for personal hygiene, it is important in order to maintain the efficiency of the wiper that the substance in question does not leak or diffuse from the tissue.

The purpose of previously known cleansing products interacting with bacteria, such as wiping cloths, is to generally inactivate or kill the bacteria. Thus, WO 8905093 discloses a wipe which releases agents for disinfection. WO 8701400 discloses a web containing an antimicrobial substance which is substantive to the fibres of the web for the purpose of preventing the diffusion of the antimicrobioal substance.

One disadvantage of such prior art cleansing products is that they can cause side-effects which in general are rapidly passing but also can be of a more serious nature. Antimicrobial substances are broad and unspecific in nature and seriously affect the normal microflora.

During the last years the binding of bacteria to carbohydrates has been a well studied phenomenon. The specific binding of type 1 piliated *E. coli* to mannose has among others been studied by Feron et al. ("Carbohydrate binding sites of the mannose-specific fimbrial lectins of enterobacteria", Infection and Immunity, vol 43, 1984, pp. 1088–90 and "Carbohydrate specificity of the surface lectins of *E. coli*, *K. pneumonia*, *S. typhimurium*", Carbohydrate Research, vol 120, 1983, pp. 235–249).

The main purpose of the present invention is to provide a new sheet of nonwoven material which makes it possible to effectively and specifically remove bacteria, especially type 1 piliated *E. coli*, in connection with the intended use, for example when wiping the hands or in connection with personal hygiene etc.

Another purpose of the invention is to provide a sheet of nonwoven material of the kind referred to, which contains an active component interacting with those bacteria which are to be removed and which thus can be said to represent the receptor for these bacteria.

Still another purpose of the invention is to provide a sheet of nonwoven material of this kind wherein the active component is represented by a carbohydrate structure.

The invention will be described in more detail below reference being made to the accompanying drawings in which.

EXAMPLE 1

Preparation of Glycosylamines

Solid ammonium bicarbonate was added until saturation to a solution of carbohydrate (50 mg) in water (2.5 ml). The mixture was stirred in an open vessel at room temperature for 3–7 days. Ammonium bicarbonate was added at intervals, saturation was assured by always keeping a portion of solid salt present in the mixture. When TLC indicated no more conversion, the mixture was diluted with water (5 ml) and concentrated to half the original volume. The residue was diluted to 20 ml with water and concentrated to 5 ml. This process was repeated once, then the residue was diluted to 10 ml and lyophilized. The crude product was purified by dissolving in water (1 ml) and passing the solution through a cation exchange resin (Bond-Elut SCX, H$^+$-form, 0.5 cartridge). After washing of the resin with water, the glycosylamine was eluted with 2M ammonia in 1:2 methanol-water (2.5 ml). The eluate was concentrated to 1 ml and then lyophilized.

4-0-(β-D-Galactopyranosyl)-β-D-glucopyranosylamine.

Treatment of lactose (50 mg) as described above gave 4-0-(β-D-galactopyranosyl)-β-D-glucopyranosylamine (41 mg, 82%) $[\alpha]_D$ +37° (c 1.0 water), $[\alpha]_D$ +38, 5° (water) NMR data: $^{13}$C, $^{\delta}$61.1 (C-6), 61.9 (C-6), 69.4 (C4), 71.8 (C-2), 73.4 (C-3), 74.8 (C-2), 76.0 (C-3), 76.2 (C-5), 76.5 (C-5), 79.5 (C-4), 85.7 (C-1), 103.7 (C-1); $^1$H δ3.20 (dd, J$_{1,2}$ 8.7, J$_{2,3}$ 9.4 Hz, H-2), 3.54 (dd, J$_{1',2'}$ 7.8, J$_{2',3'}$ 9.9 Hz, H-2), 3.55 (ddd, J$_{4,5}$ 9.6, J$_{5,6a}$ 5.0, J$_{5,6b}$ 2,3 Hz, H-5), 3.62(dd,J$_{2,3}$ 9.4, J$_{3,4}$ 8.7 Hz, H-3), 3.64 (dd, J$_{3,4}$ 8.7, J$_{3,4}$ 8.7, J$_{4,5}$ 9.6 Hz, H-4), 3.56 (J$_{2',3'}$9.9, J$_{3',4}$ Hz, H-3), 3.72 (ddd, J$_{4',5'}$1.1, J$_{5',6'a}$ 3.8, J$_{5',6'b}$ 8.1 Hz, H-5), 3.75 (dd, J$_{6',6'a}$ 3.8, J$_{6a, 6b}$ 11.6 Hz, H-6a), 3.78 (dd, J$_{5, 6a}$ 5.0, J$_{6a, 6b}$ 12.1 Hz, H6a), 3.79 (dd, J$_{5', 6'b}$ 8.1 (J$_{6'a, 6'b}$ 11.6 Hz, H-6b), 3.92 (dd, J$_{3',4'}$ 3.4, J$_{4', 5'}$ 1.1 Hz, H-4), 3.94 (dd, J$_{5,6b}$ 2.3, J$_{6a,6b}$ 12.1 Hz, H-6b), 4.11 (d, J$_{1,2}$ 8.7 Hz, H-1), 4.45 (d, J$_{1',2'}$ 7.8 Hz, H-1).

Anal. calcd. for C$_{12}$H$_{23}$NO$_{10}$xH$_2$O: C, 40.1; H, 7.0; N, 3.9. Found: C, 40.3; H, 6.8; N,3.8. A FAB-MS spectrum showed an M+1 ion at m/z 342.

EXAMPLE 2

N-Acryloylation of Glycosylamines

Sodium carbonate (100 mg) and methanol (1.0 ml) were added to a solution of the glycosylamine (0.14 mmol) in water (1.0 ml). The mixture was stirred at 0° C. while acryloyl chloride (60 μl, 0.74 mmol) in tetrahydrofuran (0.5 ml) was added during 5 min. After 10 min, the solution was diluted with water (3 ml) and concentrated to 2 ml. The solution was again diluted with water (2 ml), 200 μl of 0.5% 2,6-di-tert-butyl-4-methylphenol in tetrahydrofuran (inhibitor solution) was added, and the solution was concentrated to 1–2 ml. This solution was applied onto a C-18 silica gel column (2.0×5.0 cm), packed in water. Elution with water gave salts, unreacted glycosylamine, and reducing sugar in the first fractions, and the desired product in the later fractions. In some cases, elution of the product was preferably speeded up by adding methanol to the eluant. The few fractions containing product were pooled, mixed with a few drops of inhibitor solution, and concentrated to 2 ml. This solution was purified by gel filtration on a Bio-Gel P2 column. Appropriate fractions were pooled and lyophilized.

N-Acryloyl-4-0-(β-D-galactopyranosyl)-3-D-glycopyranosylamine:

Treatment of 4-0-(β-D-Galactopyranosyl)-β-D-glucopyranosylamine (50 mg) with acryloyl chloride (60 ml) as described above gave N-acryloyl-4-0-(β-D-galactopyranosyl)-3-D-glycopyranosylamine (51 mg, 88%), $[α]_D$ −7° (c 0 5, water). NMR data: $^{13}$C, δ60.7 (C-6) 61.9 (C-6), 69.4 (C-4), 71.8 (C-2), 72.3 (C-2), 73.3 (C-3), 75.9 (C-3), 76.2 (C-5), 77.3 (C-5), 78.6 (C-4), 80.1 (C-1), 103.7 (C-1), 130.20, 130.25 (CH=CH$_2$), 170.2 (C=O); 1, δ3.49 (dd $J_{1,2}$ 9.2 Hz, H-2), 3.56 (dd, $J_{1',2'}$ 7.8, $J_{2',3'}$ 9.9 Hz, H-2), 3.67 (dd, $J_{2',3'}$ 9.9, $J_{3',4'}$ 3.4 Hz, H-3), 3.70 (m, H-5), 3.72 (m, H-3), 3.73 (m, H-4), 3.75 (m, H-5), 3.77 (dd, $7_{5'6'b}$ 3.8, $J_{6'a, 6'b}$ 11.6 Hz, H-6b), 3.80 (dd, $J_{5',6'a}$ 8.2, $J_{6'a,6'b}$ 11.5 Hz, H-6a), 3.82 (dd, $J_{5,6b}$ 4.4 $J_{6a,6b}$ 12.3 Hz, H-6b), 3.93 (dd, $J_{3',4}$ 3.4, $J_{4',5}$ 1.6 Hz, H-4), 3.94 (dd, $J_{5,6a}$ 2.1, $J_{6a,6b}$ 12.3 Hz, H-6a), 4.46 (d, $J_{1',2'}$ 7.8 Hz, H-1), 5.08 (d, $J_{1,2}$ 9.2 Hz, H-1) 5.87 (dd, J 3.7 and 7.9 Hz, CH=CH$_2$).

Anal. Calcd. for $C_{15}H_{25}NO_{11}$: C, 45.6; H, 6.4; N, 3.5. Found: C, 41.1; H, 6.1; N, 3.6.

EXAMPLE 3

Copolymerization of N-acryloylglycosylamines with acrylamide.

A solution of the N-acryloylglycosylamine (52 μmol) and acrylamide (210 μmol, 15 mg) in distilled water (400 μl) was deaerated by flushing with nitrogen for 20 min. The solution was then stirred at 0° C. and N,N,N',N'-tetramethylethylenediamine (2 μl) and ammonium persulfate (1 mg) were added. The mixture was slowly stirred at 0° C. for 2 h, and then at room temperature overnight. The viscous solution was diluted with water (1 ml) and purified by gel filtration on Fractogel HW 55 (F). Fractions containing polymer were pooled and lyophilized.

Copolymer of N-Acryloyl-4-0-(β-D-galactopyranosyl)-β-D-glucopyranosylamine and acrylamide:

Treatment of N-acryloyl-4-0-(β-D-galactopyranosyl)-3-D-glycopyranosylamine (20 mg) with acrylamide (7.2 mg, 2 eq) as described above gave copolymer (18 mg, 54% calculated from 3), $[α]_D$+7° (c 0.1, water). Analysis of the material by $^1$H NMR spectroscopy (D$_2$O, 50° C.) showed presence of approximately 1 lactose unit per 4.6 CHCH$_2$ units (theoretical value: ⅓). The molecular weight distribution of the copolymer, as determined by gel filtration, was 50–1000 kDa, centered around 300 kDa.

For further details of the technique for such copolymerization procedures the published Swedish patent application 463314 is referred to, the disclosure of which is incorporated herein by reference.

EXAMPLE 4

Coupling of Mannoside to Fractogel.

Aldehydo Fractogel TSK HV 65(F) (100 g) in a moist, filtered state (0.1M KH$_2$PO$_4$, adjusted with NaOH or HCl to pH 7), 10 μmol p-aminophenyl-α-D-mannopyranoside (A 1394, Sigma), 630 mg NaCNBH$_3$ (10 μmol) and 250 mg NaBH$_4$ were used as starting materials for the coupling reaction.

The fractogel was thoroughly dewatered and placed in a suction flask, and 0.1M phosphate buffer, pH 7 (400 ml), the mannopyranoside and the sodium cyanoborohydride was added. The flask was placed on a shaking table and a suspension was achieved by starting the shaking table. The reaction was allowed to proceed for about 4 days at room temperature.

Excess formyl groups were then destroyed by the careful addition of sodium borohydride and the contents of the flask were then shaken for another hour. The gel was filtered off and thorougly washed with water. Then the gel was shaken in clean water for another hour before it was finally filtered off. The prepared gel was stored in a 25% ethanol solution.

The structure of the mannose substituted fractogel schematically can be illustrated in the following way:

(I)

EXAMPLE 5

Binding of E. coli to Mannose Substituted Fractogel

Fifty μl of E. coli KSKP 373, 382 and 395, respectively, labelled with radioactive iodine was added to 1.5 ml phosphate buffered saline (PBS). To 0.2 ml of each bacterial suspension 0.2 ml of substituted and unsubstituted fractogel, respectively, was added. The suspensions were allowed to be incubated for 30 min on a shaking table and were then centrifuged for 10 min at 500 rpm. The supernatant was decanted off and the radioactivity in the fractogel was measured before washing, after washing with PBS, and after two washings with PBS. In the present experiment the E. coli strains KSKP 373 and 382 were type 1 piliated while KSKP 395 lacks the type 1 pili. The results are presented in Table I below.

TABLE I

|  | E. coli strain | Before washing | After first washing | After second washing |
|---|---|---|---|---|
| Control gel | KSKP 373 | 1841469 | 193567 | 86162 |
|  |  | 18884026 | 206900 | 84472 |
|  |  | 1682612 | 199781 | 100471 |

TABLE I-continued

| | E. coli strain | Before washing | After first washing | After second washing |
|---|---|---|---|---|
| Substituted gel | KSKP 373 | 1900011 | 434393 | 272106 |
| | | 2030421 | 428443 | 264717 |
| | | 2265375 | 460703 | 239423 |
| Control gel | KSKP 382 | 1373657 | 189580 | 115216 |
| | | 1524220 | 194324 | 103543 |
| | | 1508750 | 233895 | 141118 |
| Substituted gel | KSKP 382 | 2478434 | 956399 | 624386 |
| | | 2110952 | 897985 | 677083 |
| | | 1973859 | 773461 | 541835 |
| Control gel | KSKP 395 | 1659411 | 252034 | 86400 |
| | | 1654242 | 222732 | 107824 |
| | | 1549139 | 164238 | 68923 |
| Substituted gel | KSKP 395 | 2133908 | 301827 | 164542 |
| | | 2287366 | 382092 | 183858 |
| | | 2677496 | 450601 | 187693 |

As was evident from the table, mannose substitution results in a considerably improved adherence of the bacteria compared with unsubstituted gel. Furthermore, it was evident from the table that bacteria with type 1 pili present a somewhat better adherence to the substituted gel than bacteria lacking such pili.

EXAMPLE 6

Preparation of a Conjugate of p-Aminophenyl-α-D-Mannopyranoside and Human Serum Albumin (HSA).

p-Aminophenyl-α-D-mannopyranoside (0.1 µmol, Sigma Chemicals) was dissolved in 0.1M phosphate buffer, pH 7.0 (50 ml), in a 50 ml conical flask and then ethanol (10 ml) was added. Then thiofosgen (0.040 ml) was added with magnetic stirring and after 10 min the magnetic bar was removed and a thorough washing was performed with distilled water (about 5 ml in total). After that, diethyl ether (about 10 ml) was added to the flask and the flask was then carefully shaken vigorously with the stopper inserted. The phases were allowed to separate and the lower water phase was then transferred to a 100 ml conical flask with a pasteur pipette. Distilled water (about 2 ml) was added to the remaining ether phase; shaking was then performed carefully and, after separaration, the new water phase was transferred to the conical flask. The conical flask was mounted on a roll evaporator and the contents were reduced to about 2 ml.

The solution obtained was added to a protein solution prepared in advance containing HSA (162.5 mg) dissolved in borate buffer (pH 9.2, 26.3 ml), the dissolution being completed after about one hour. The pH was then adjusted to 9.5 with a 2M solution of NaOH. The mixture was allowed to stand overnight with slow stirring and the pH was controlled to lie within the interval 8.5 to 9.5. The reaction progress was controlled by TLC. The reaction mixture was transferred to an ultrafilter which was filled with 10 to 150 ml distilled water. Ultrafiltration was performed until only some ten milliliters remained, refilling and then filtration was performed, after that another refill and filtration down to a couple of milliliters. The mixture was filtered through glass wool into a preweighed jar, whereupon lyophilization was performed.

The contents of the conjugate was determined either by sugar analysis or colorimetrically.

EXAMPLE 7

Binding of E. coli to a Paper Towel Coated with HSA-Conjugate.

The same E. coli strains as in Example 4 were used in these experiments. Substituted and unsubstituted HSA, respectively, was dissolved in PBS (1 mg/ml). 10 µl of each solution was applied on a piece of paper punched out from a paper towel of standard quality with a perforator. When the paper had become dry 100 µl suspension of bacteria was added to the piece of paper in a test tube and incubation was performed for 30 min at 37° C. The radioactivity was then recorded in a gamma counter and the piece of paper was washed twice with PBS. The recording in such a gamma counter was performed before the washing and after each washing. The results are shown in Table II below.

The conjugate in question between mannoside and HSA can be illustrated in the following way:

(II)

TABLE II

| | E. coli strain | Before washing | After first washing | After second washing |
|---|---|---|---|---|
| HSA-paper (control) | KSKP 373 | 36937 | 12773 | 5645 |
| | | 33563 | 12945 | 5982 |
| Substituted HSA-paper | KSKP 373 | 46562 | 14654 | 8288 |
| | | 42882 | 18616 | 9432 |
| HSA-paper (control) | KSKP 382 | 19113 | 13211 | 9341 |
| | | 19563 | 14647 | 10842 |
| Substituted HSA-paper | KSKP 382 | 48301 | 24067 | 15896 |
| | | 33093 | 22485 | 17597 |
| HSA-paper (control) | KSKP 395 | 16082 | 12102 | 4337 |
| | | 16164 | 7915 | 4579 |
| Substituted HSA-paper | KSKP 395 | 13819 | 7447 | 4400 |
| | | 14207 | 8709 | 4640 |

These experimental results also confirm that mannoside substitution entails a considerable improved adherence to the paper.

EXAMPLE 8

Synthesis of 4-Acryloylamidophenyl-α-D-Mannopyranoside.

A solution of 4-aminophenyl-α-D-mannopyranoside (1.4 mmol, 170 mg) in a mixture of water (10 ml) and methanol (20 ml) was stirred while sodium carbonate (1000 mg) was added. The mixture was then cooled to 0° C. and acryloyl chloride (600 µl, 7.4 mmol) in tetrahydrofuran (5 ml) was added during 5 min. After 10 min, the solution was diluted with water (30 ml) and concentrated to 10 ml. The solution was applied onto a C-18 silica gel column (5×30 cm) and the column was eluted first with water, then with methanol-water mixtures of increasing methanol content. The fractions containing the desired product (by TLC) were pooled and concentrated. The yield was 360 mg (80%).

EXAMPLE 9

Synthesis of Copolymer 4-Acryloylamido-α-D-Mannopyranoside/Acrylamide (ratio 1:4).

A solution of 4-acryloylamidophenyl-α-D-mannopyranoside (160 mg, 0.5 mmol) and acrylamide (150 mg, 21 mmol) in distilled water (4 ml) was deaerated by flushing with nitrogen for 20 min, then stirred at 0° C. while N,N,N',N'-tetramethylethylenediamine (20 μl) and ammonium persulfate (10 mg) were added. The mixture was slowly stirred at 0° C. for 2 h, then at room temperature overnight. The viscous solution was diluted with water (10 ml) and purified by membrane filtration against distilled water. Lyophilization of the high-molecular retentate gave polymer (160 mg), the carbohydrate content of which was determined with the phenol-sulfuric acid colorimetric assay.

EXAMPLE 10

Synthesis of Copolymer 4-Acryloylamidophenyl-α-D-Mannopyranoside/Acrylamide (Ratio 1:10).

A solution of 4-acryloylamid α-D-mannopyranoside (65 mg, 0.2 mmol) and acrylamide (150 mg, 2.1 mmol) in distilled water (4 ml) was deareated by flushing with nitrogen for 20 min, then stirred at 0° C. while N,N,N',N'-tetramethylethylenediamine (20 μl) and ammonium persulfate (10 mg) was added. The mixture was slowly stirred at 0° C. for 2 h, then at room temperature overnight. The viscous solution was diluted with water (10 ml) and purified by membrane filtration against distilled water. Lyophilization of the high-molecular retentate gave polymer (110 mg), the carbohydrate content of which was determined with the phenol-sulfuric acid colorimetric assay.

EXAMPLE 11

Synthesis of Copolymer 4-Acryloylamidophenyl α-D-Mannopyranoside/Acrylamide (Ratio 1:20), A solution of 4-acryloylamid α-D-mannopyranoside (32 mg, 0.1 mmol) and acrylamide (150 mg, 2.1 mmol) in distilled water (4 ml) was treated as above. Lyophilization of the high-molecular retentate gave polymer (100 mg), the carbohydrate content of which was determined with the phenol-sulfuric acid colorimetric assay.

EXAMPLE 12

Method of Manufacturing Sheets of Nonwoven Material

The active component of the sheet according to the invention is integrated by mixing of a composite material comprising for example cellulose and/or regenerated cellulose and a synthetic copolymer in which the carbohydrate structure was included. Such a copolymer can be constructed with a mannose derivative and an amide as starting materials. Preferably, the copolymer has the formula:

$$\begin{bmatrix} CONHR^2 & CONH_2 \\ | & | \\ C-CH_2-(C-CH_2)_x \\ | & | \\ R^3 & R^3 \end{bmatrix}_m \quad (III)$$

in which $R^2$ has the formula:

(IV)

$R^3$ was H or $CH_3$;
x was an integer from 0 to about 20; and m was such that the molecular weight of the copolymer is from about 5 to about 2000 kDa.

Thus, m was chosen in order to give the copolymer a molecular weight of from about 5 to about 2000 kDa. By assigning x an integer from 2 to about 40, different ratios was obtained between α-D-mannopyranoside compound and acrylamide.

An especially preferred mannose derivative for use in such a copolymerization has the formula:

in which $R^2$ and $R^3$ have the meanings mentioned above.

Thus, when manufacturing sheets of nonwoven material according to the present invention fibers of cellulose and/or rayon are initially arranged at random with a copolymer mixture comprising a carbohydrate derivative copolymerized with acrylamide. The nonwoven material was made up of substantially 5 to substantially 50% by weight, preferably 40% by weight, of cellulose, substantially 5 to substantially 50% by weight, preferably 40% by weight, of rayon (regenerated cellulose) and substantially 5 to substantially 40% by weight, preferably 20% by weight, of copolymer mixture. The copolymer mixture comprises a copolymer of polyvinylacetate-polythylene and between 0 and 50% by weight, preferably 5%, of copolymerized carbohydrate derivative, preferably 4-acryloylamidophenyl-α-D-mannopyranoside, with acrylamide in different ratios. The different ratios of the copolymer 4-acryloylamidophenyl-α-D-mannopyranoside/acrylamide are obtained by mixing the correct amounts of acryloylamidophenyl-α-D-mannopyranoside and acrylamide, respectively.

The function of the copolymer was to bind cellulose and rayon fibers and was a standard operating procedure in the production of nonwoven material. The process of combining fibers was according to known techniques accomplished by a rapid increase of temperature by which the copolymers "melt" and adhere to the fibers. This was for example achieved by a high-temperature calendaring operation which was accomplished by passing the web between two hot rollers whereby a sheet is obtained. Such sheets are then used as tissues for wiping for example the hands, in connection with personal hygiene, or the like.

EXAMPLE 13

Sugar Analyses of Extracts of Tissues with Mannose Polymer and Extracted in a Saline Solution.

An experiment was conducted by incubation of pieces (about 30 mg each) of nonwoven tissue in 1 ml of saline for 15 days.

The extracts were analysed for sugars according to Sawardeker et al. In brief, hydrolysis was done in 2M trifluoroacetic acid. The released monosaccharides were reduced with sodium borohydride and converted to their corresponding alditol acetates and finally analysed in a HP 5970 gas chromatography-masspectrometric system.

Figure 1A:
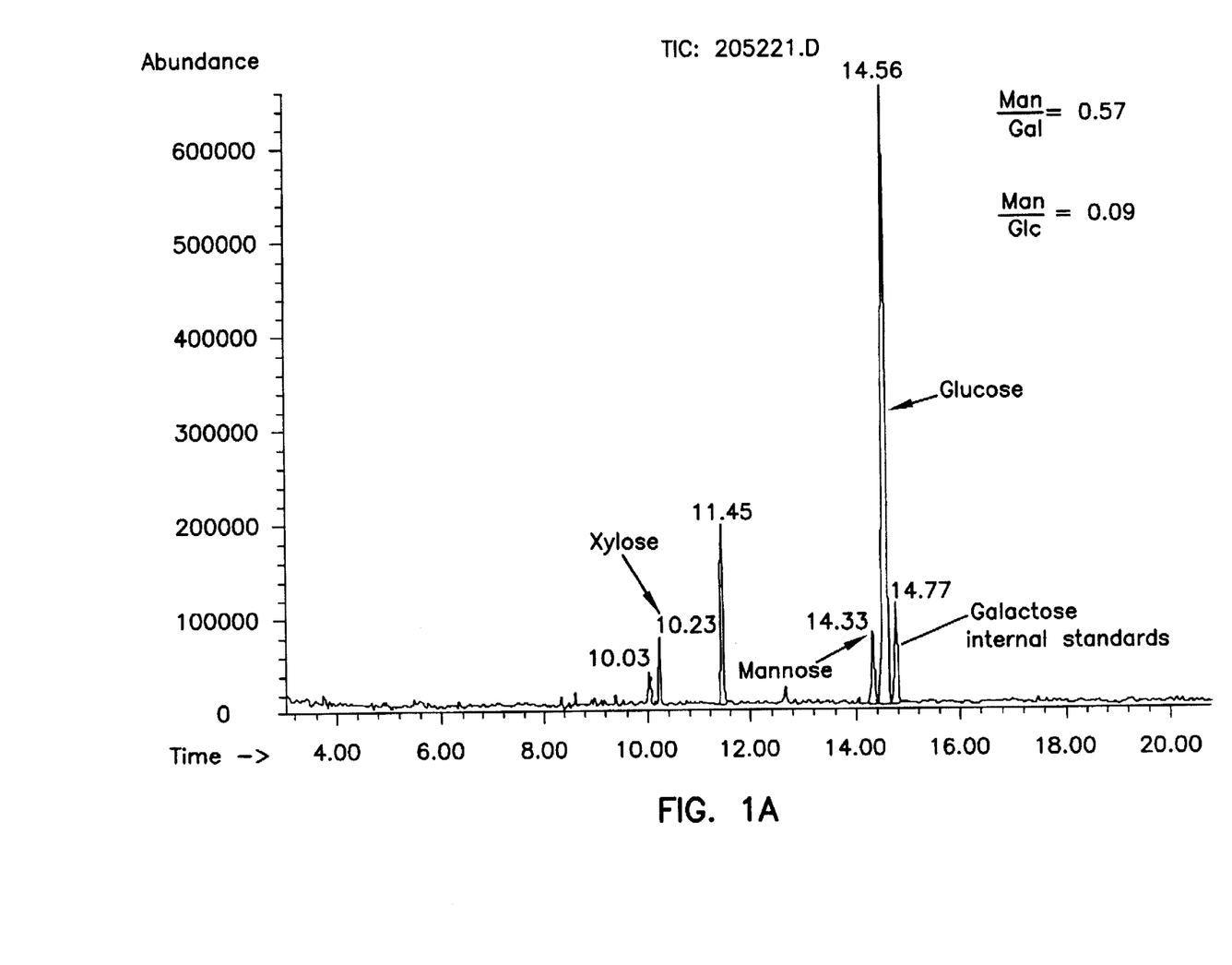
FIG. 1 shows the identification by mass spectrometry of sugar peaks in the gaschromatogram of extracts of tissues with incorporated mannose polymer and extracted in a saline solution.
Figure 1B:
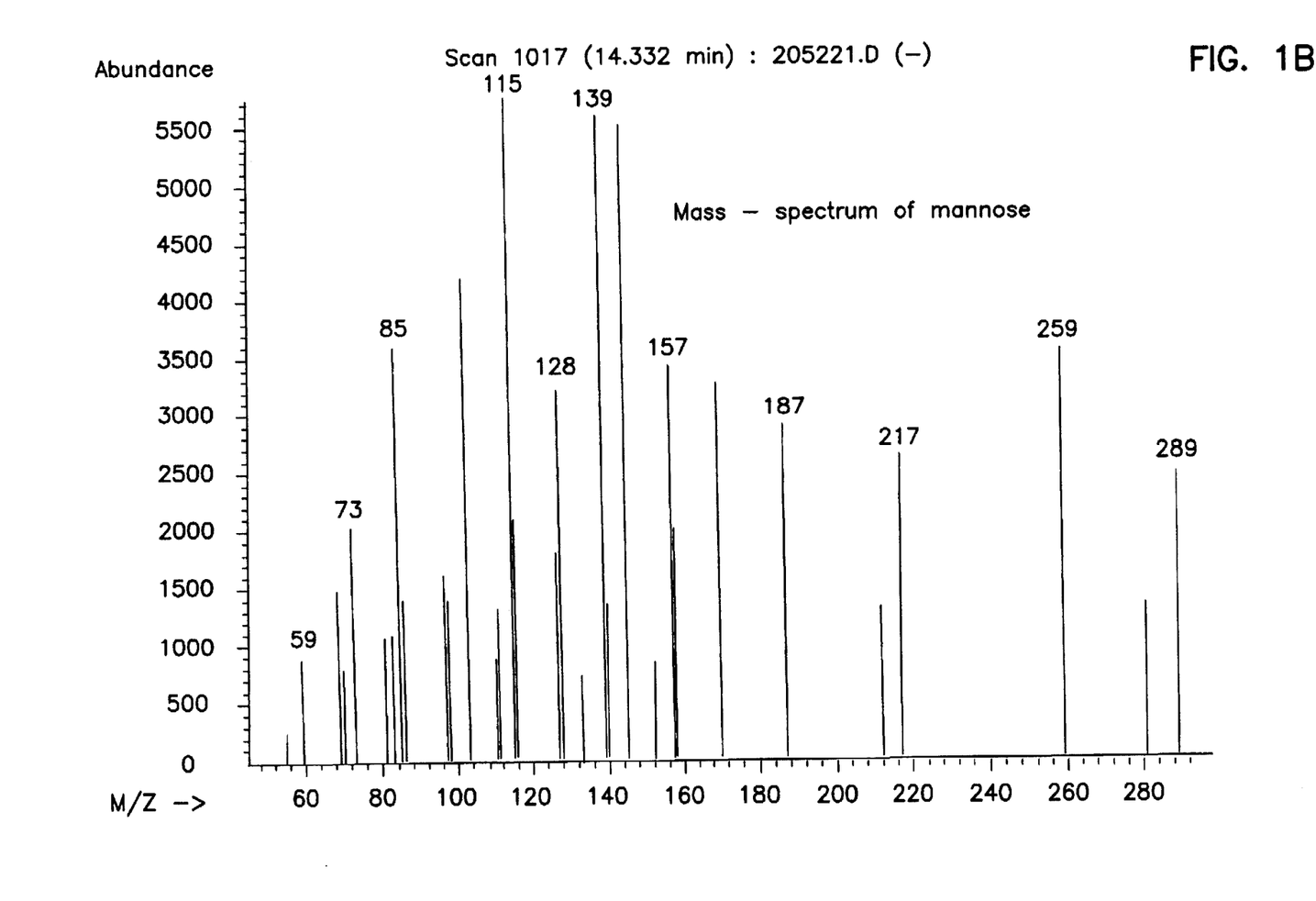

The amount of mannose present in unsubstituted nonwoven tissue was estimated to be approximately 0.13 μg/mg. Galactose was used as internal standard since no galactose was found as background component, and nothing else eluted with the same retention time. Xylose and glucose were also identified in this material. (FIG. 1, top). The sugar peaks in the gaschromatogram were all identified with mass spectra (FIG. 1, bottom).

Figure 2A:
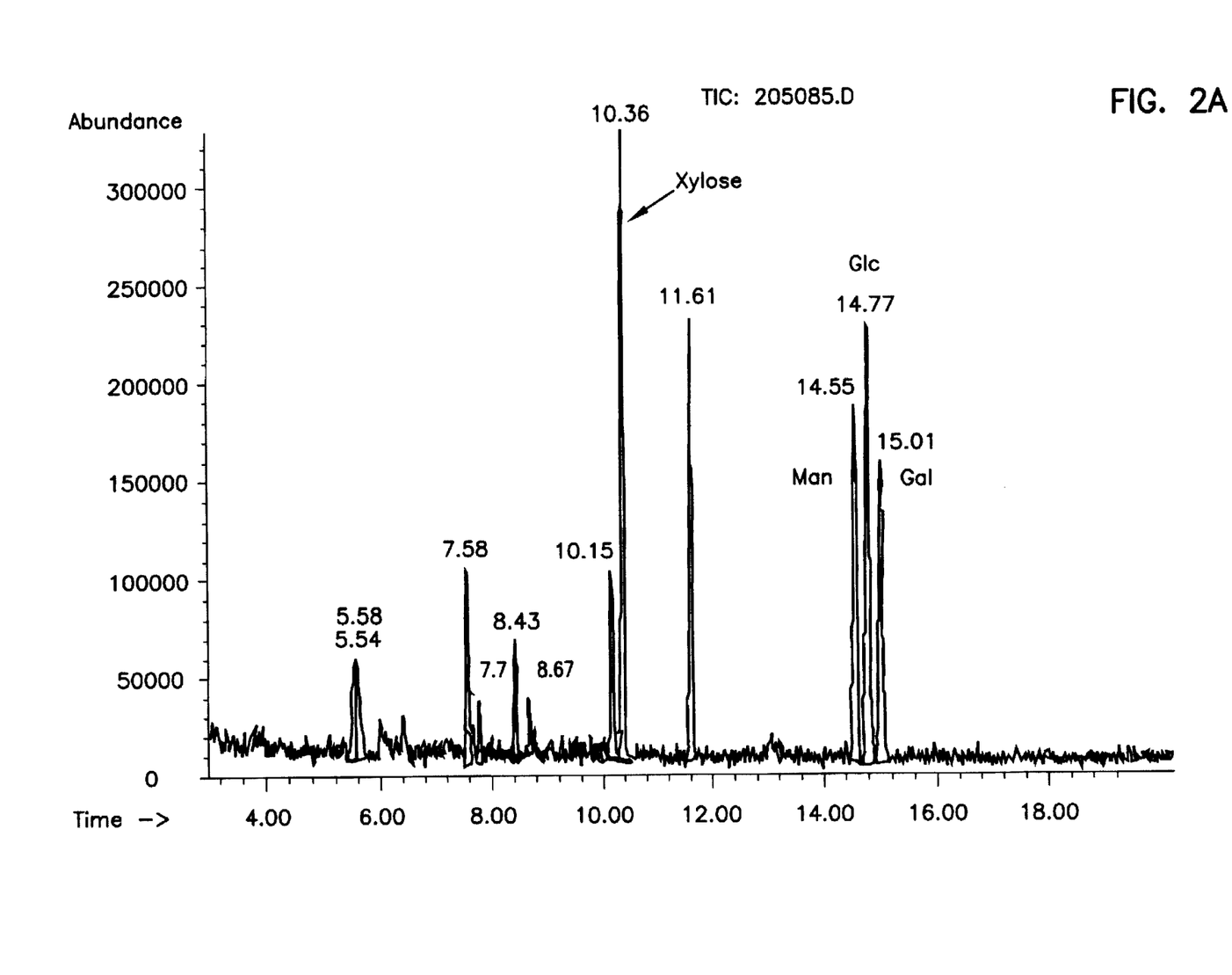
FIG. 2 shows the identification by mass spectrometry of sugar peaks in the gaschromatogram of extracts of tissues with incorporated mannose polymer and wrapped in "Carefree"-tissues.
Figure 2B:
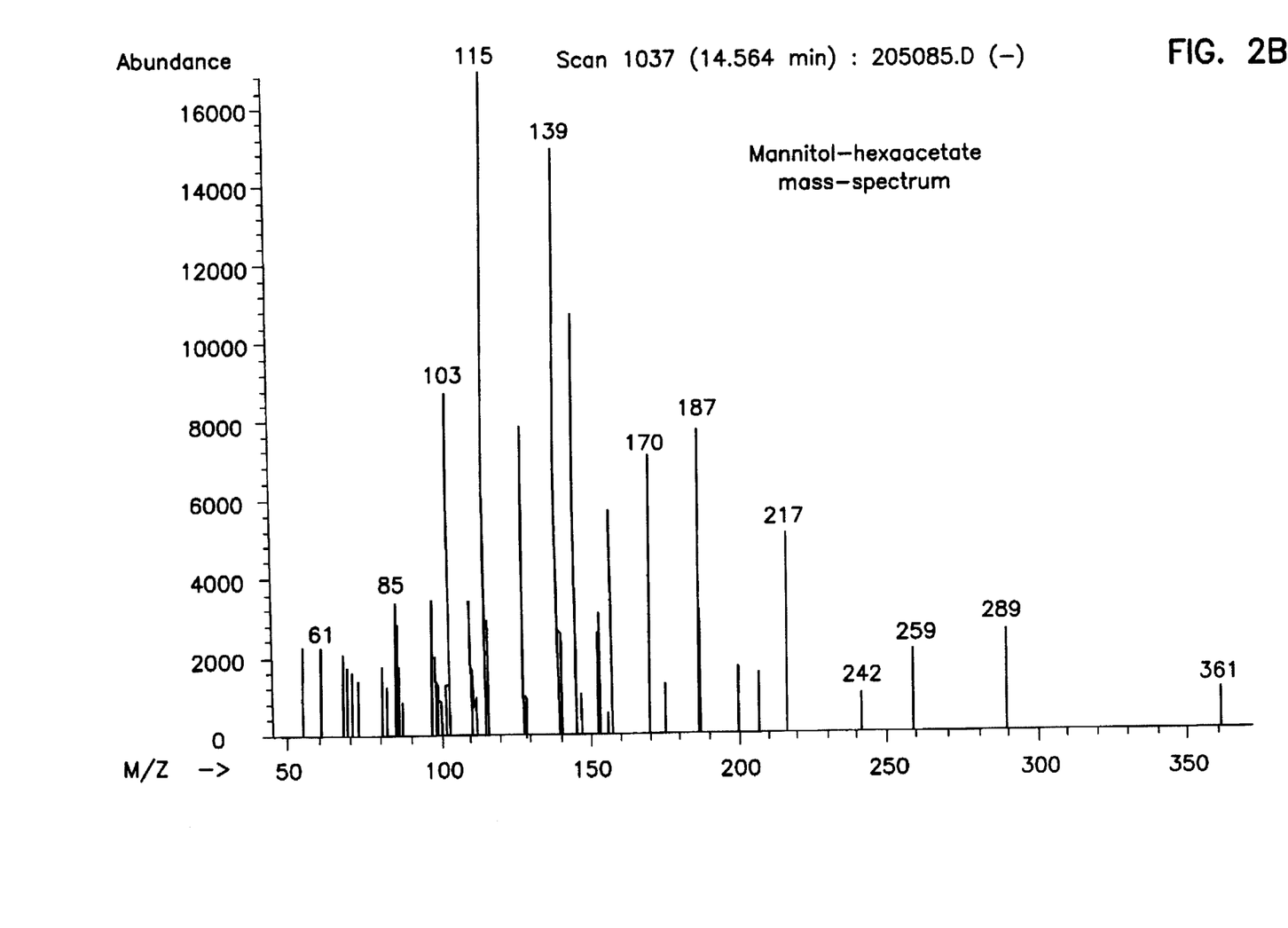

The corresponding amount of mannose in the 5% mannose-polymer substituted nonwoven tissue was 0.2 µg/mg (FIG. 2).

EXAMPLE 14

Sugar Analyses of Extracts of Tissues with Incorporated Mannose Polymer and Wrapped in "Carefree"-Tissues In another experiment the amount of mannose present in extract of 5% mannose polymer substituted nonwoven tissue wrapped in "Carefree"-tissues was determined. Pieces of nonwoven tissue (about 30 mg each) were wrapped in the wet-tissue ("Carefree") and incubated for 1, 3 and 7 days in sealed test tubes. After incubation 1 ml of saline was added and the content of the tube was transferred to Centriflow membrane cones (Millipore), centrifuged and the centrifugate was submitted to sugar analyses as described above.

Figure 3:
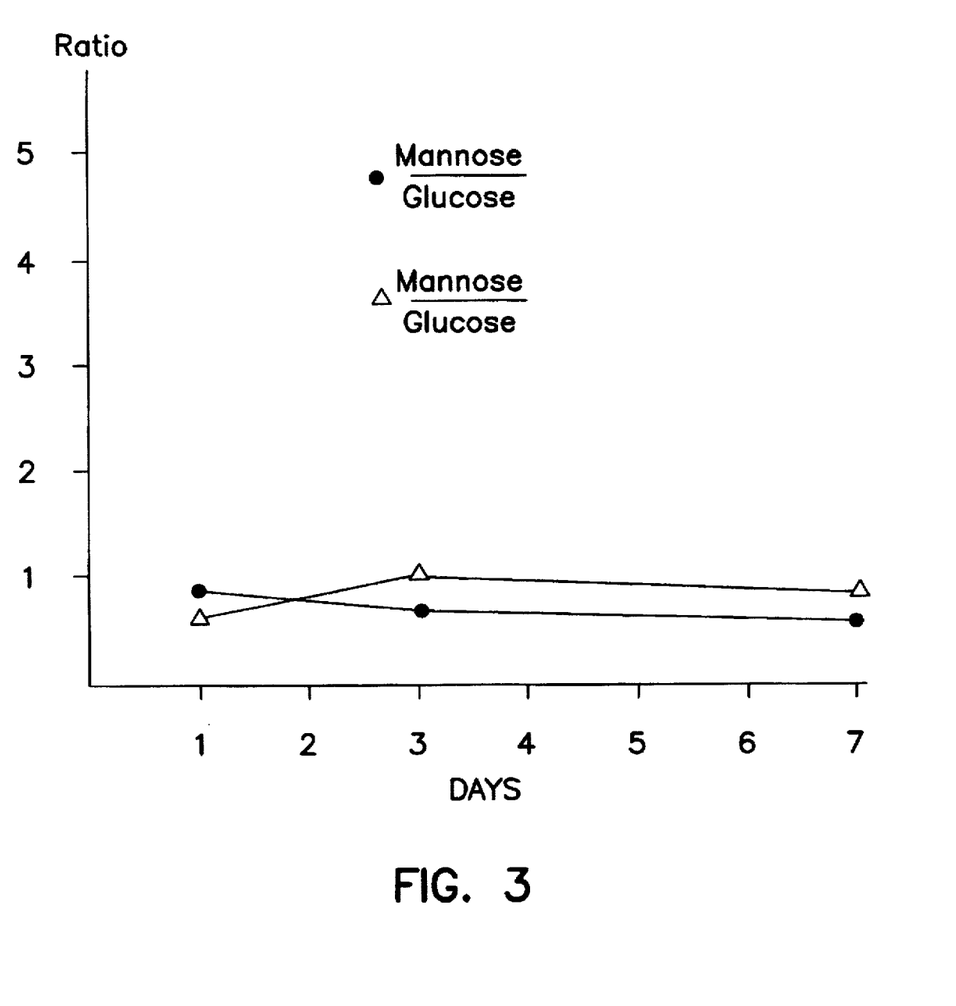
FIG. 3 shows monosaccharide ratios of such extracts at different incubation periods.

Approximately the same amount (0.2 µg/mg tisssue) was found in these extracts as in the extracts of Example 13. No difference in ratios mannose/glucose or mannose/galactose was seen in the 1, 3 and 7 days samples. (FIG. 3).

It should be noted that small amounts of xylose, glucose as well as mannose containing material was present as a natural content of these tissues.

EXAMPLE 15

Binding in Vitro of E. Coli to Nonwoven Tisssue Substituted with Different Concentrations of Mannoside Nonwoven tissues containing different concentrations of mannoside (i.e. different ratios of copolymer 4-acryloylamido-α-D-mannopyranoside/acrylamide) were cut in confetti-sized discs with a paper perforator.

E. coli bacteria were grown overnight statically in RPMI-medium (Flow) or in nutrient broth in the presence of $^3H$ thymidine (1 µCi/ml) (Amersham).

The bacteria were washed twice and resuspended in phosphate buffered saline (PBS) in a concentration of $10^{9/}$ml.

One tissue disc in 50 µl PBS was mixed with 100 µl of bacterial suspension ($10^8$). The mixture was incubated 30 min at 37° C. Thereafter the tissue disc was collected and washed in 2 ml of PBS.

Finally, the disc was dried and transferred to scintillation vials containing 2 ml of Insta-Fluor scintillation liquid (Packard).

The radioactivity=bacteria bound to tissue discs was measured in a scintillation counter (LKB-Wallac). Radioactivity (cpm) per bacterium was calculated from seperate experiments.

All experiments were performed in triplicate. The variability within triplets was always less than 15% with more than 5% mannoside in the tissues.

Figure 4A:
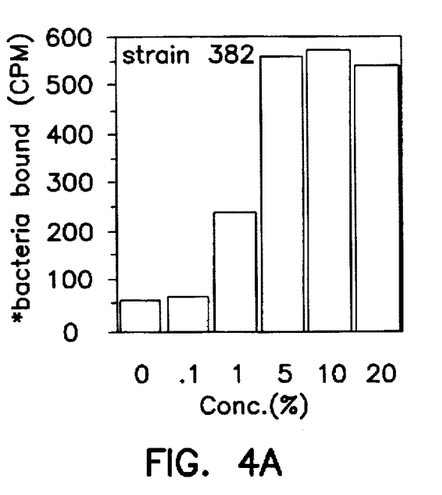
FIG. 4 shows the binding of *E. coli* laboratory strains to discs of nonwoven tissue with different concentrations of mannose substitution.
Figure 4B:
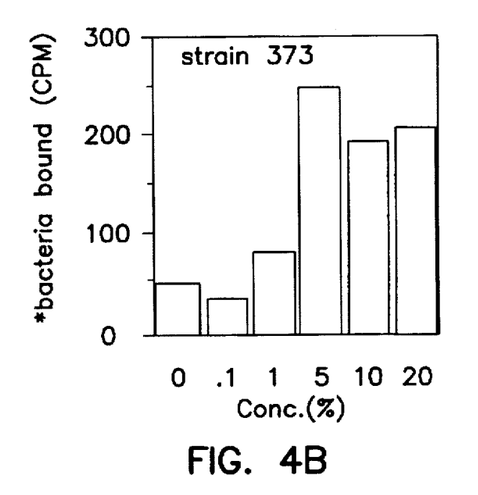
Figure 4C:
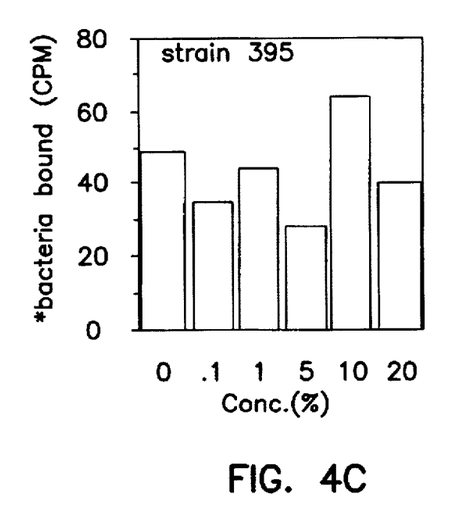

As shown in FIG. 4, two piliated (type 1) E. coli strains 382 and 373 bind strongly to mannoside substituted nonwoven tissue. Optimal binding was reached at 5% mannoside. In contrast the non-piliated strain 395 binds only very weakly to the tissue.

Figure 5A:
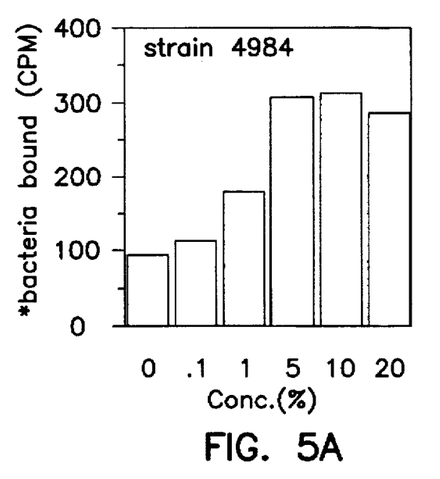
FIG. 5 shows the binding of *E. coli* clinical isolates to discs of nonwoven tissue with different concentrations of mannose substitution.
Figure 5B:
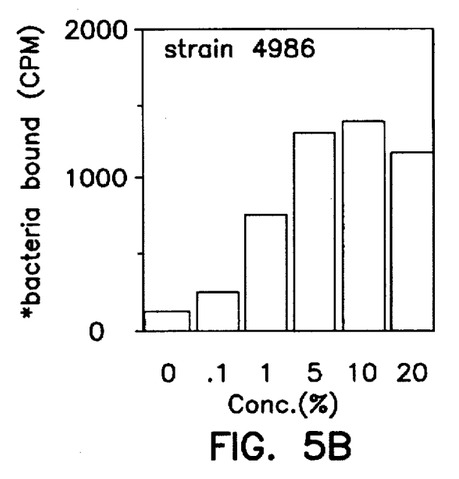
Figure 5C:
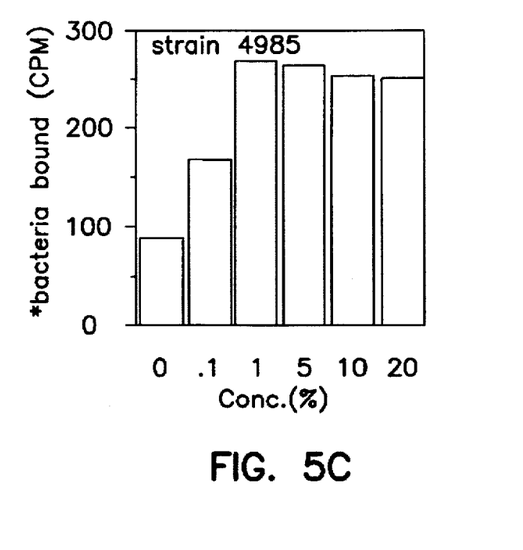

FIG. 5 shows that also clinical isolates of E. coli bind strongly to 5% mannoside tissue.

EXAMPLE 16

Binding of Different E. coli Bacteria to Confetti Sized Nonwoven Discs Not Substituted or Substituted with 5% Mannoside The binding of different E. coli bacteria to confetti sized (5.5 mm diameter) nonwoven discs not substituted (0%) or substituted with 5% mannoside was investigated as in Example 15.

The number of bacteria has been calculated from cpm-data. Table III shows that tissue substituted with 5% mannoside bind type 1 pili positive and clinical isolates of E. coli approximatively 10 times better than nonsubstituted tissue. However, the type 1 negative strain 395 binds only weakly to both tissues.

TABLE III

| Strain | Bacteria/0% mannoside | Bacteria/5% mannoside |
|---|---|---|
| 395 (neg) | 80,940 | 126,664 |
| 382 (pos) | 475,416 | 6,403,632 |
| 47 (clin) | 2,276,820 | 21,185,580 |
| 192 (clin) | 670,340 | 6,525,772 |
| 195 (clin) | 1,133,050 | 5,664,400 |

EXAMPLE 17

Electronmicroscopy Studies

Nonwoven tissue substituted with mannoside or nonsubstituted was tested for binding of E. coli. After incubation with bacterial suspensions ($10^9$/ml) the tissue was washed and investigated by electron microscopy.

Figure 6A:
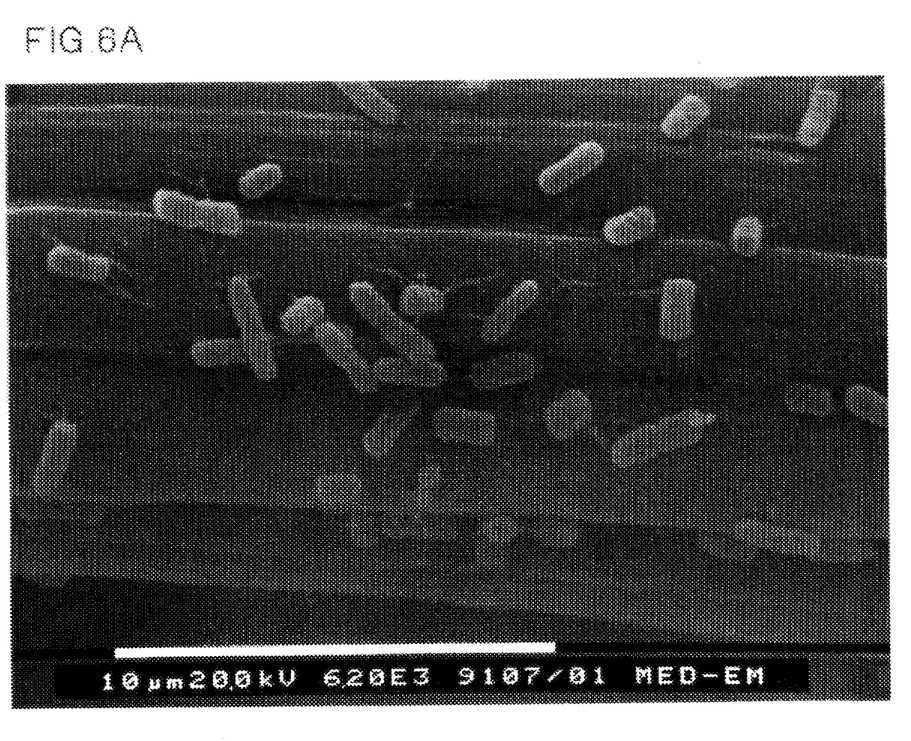
FIG. 6 shows electron microscopy pictures of *E. coli* bacteria bound to nonwoven tissue substituted with mannoside.
Figure 6B:
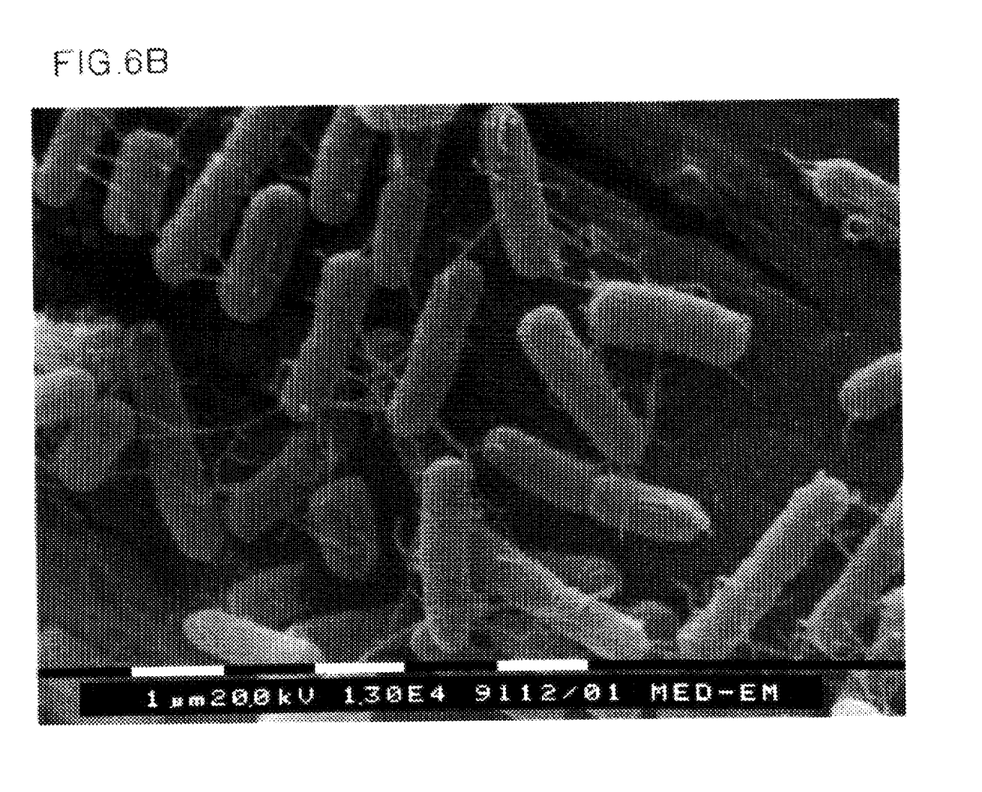
Figure 7A:
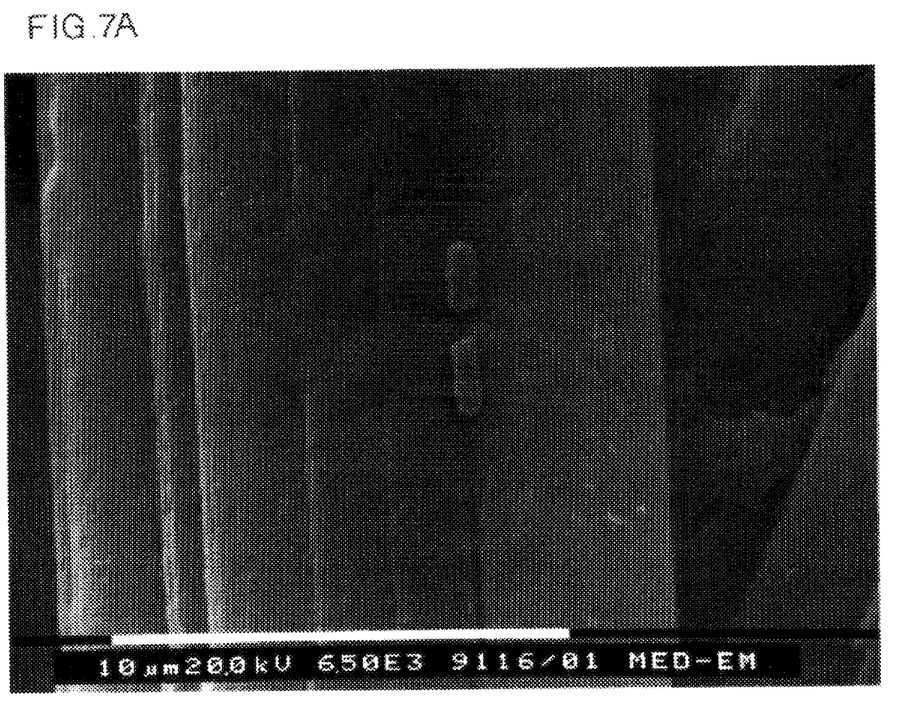
FIG. 7 shows electron microscopy pictures of *E. coli* bacteria bound to unsubstituted nonwoven tissue.
Figure 7B:
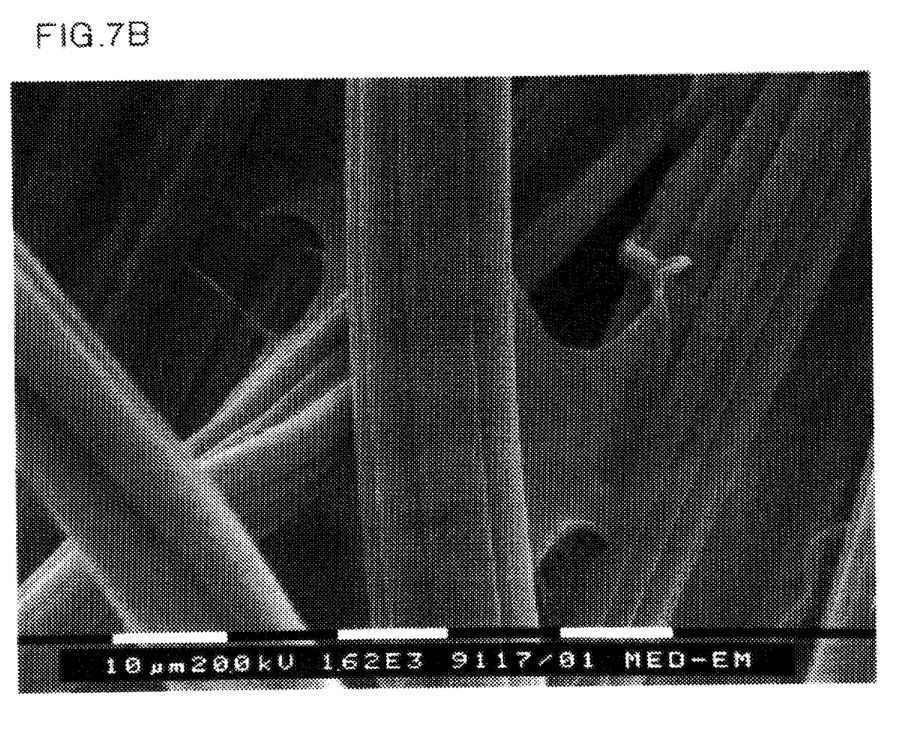

The experiments showed that mannoside tissue bound very high numbers of E. coli as exemplified by pictures 9107 and 9112 (FIG. 6). However, type 1 negative bacteria could not be detected on the mannosidic tissue. For the reference tissue no or only very few bacteria could be detected irrespective of piliated or non-piliated bacteria were studied. This is exemplified by pictures 9116 and 9117 (FIG. 7).

EXAMPLE 18

Evaluation of the Count of Skin Areas Seeded with Type 1 Pili Positive E. coli An in vivo experiment was performed to evaluate whether mannoside tissues significantly reduce the count of skin areas seeded with type 1 pili positive E. coli A type 1 piliated E. coli, strain 382, was used as test microorganism and incubated in static TSB at 35° C. Test patches of 6 cm×6 cm from a test tissue substituted with 5% mannoside and a unsubstituted reference sheet respectively, were wetted with 3× weight of sterile water overnight.

The right arm of a healthy volunteer was seeded in three marked areas with strain 382 and the areas were allowed to dry. The test tissue patch was applied to one area, the reference patch to the second, and the third area was used as positive control. After a contact time of one min both tissue patches were removed. All areas were then swabbed with a moistened swab, and counts were performed on each swab. The results are shown in Table IV below.

TABLE IV

| Swab from | No of bacteria |
|---|---|
| Test tissue area | $6.4 \times 10^4$ |
| Referenc tissue area | $3.8 \times 10^5$ |
| Positive control | $1.6 \times 10^6$ |

As shown in Table IV the application of the reference tissue to seeded areas reduces the E. coli counts by approximaively 5 times. The application of a mannoside tissue reduces this count 5 times.

Thus, mannoside tissue was more effective also in vivo.

The cleansing product according to the invention can exist in form of a napkin or a product roll such as toilet paper but it can also consist of a so called wet wipe which then suitably is enclosed in a sealed envelope.

It has thus been shown that by incorporating a derivative of D-mannose into wet tissues the capacity of these wet tissues to bind *E. coli* and other Enterobacteriacae can be increased ten times. Thus, by the incorporation of a D-mannose derivative into wet tissues these can be used for removal of UTI-causing bacteria from the periurethral tract. The usage of this type of wet tissue might also significantly improve the genital hygiene of women and young children. In addition, nonwoven tissue containing D-mannose can be incorporated in all kinds of diapers for infants, woman and in eldercare to prevent urinary tract infections.

The invention is not limited to the embodiments described and shown in detail since different modifications can be made without departing from the scope of the invention. The invention is intended to be used in all such cases where a sheet shall have the ability of removing not only bacteria but also virus from a cleaning site. Thus, the sheet of the kind mentioned above can be utilized for removing or trapping influenza virus if sialic acid is used as a carbohydrate N-acryloyl glycosylamine copolymerized with acrylamide.

We claim:

1. A sheet of nonwoven material comprising:
   fibers arranged at random and a copolymer;
   the copolymer comprising a 4-acryloylamido-phenyl-α-D-mannopyranoside copolymerized with acrylamide;
   the copolymer and fibers being mixed and heat treated to form a sheet of nonwoven material in which the copolymer is carried by the fibers; and the sheet being effective to remove bacteria from a site to be cleaned.

2. The sheet of claim 1, wherein the fibers are cellulose or rayon, and the copolymer further comprises vinylacetate and ethylene.

3. The sheet as in claim 2, wherein the amount of cellulose ranges from substantially 5% to substantially 50% by weight.

4. The sheet of claim 3, wherein the amount of cellulose is about 40% by weight.

5. The sheet of claim 2, wherein the amount of rayon ranges from substantially 5% to substantially 50% by weight.

6. The sheet of claim 5, wherein the amount of rayon is about 40% by weight.

7. The sheet of claim 2, wherein the amount of copolymer ranges from substantially 5% to substantially 40% by weight.

8. The sheet of claim 7, wherein the amount of copolymer is about 20% by weight.

9. The sheet of claim 1, wherein the ratio of 4-acryloylamido-phenyl-α-D-mannopyranoside to acrylamide is between 1:2 and 1:40.

10. The sheet of claim 9, wherein the ratio of 4-acryloylamido-phenyl-α-D-mannopyranoside to acrylamide is about 1:5.

11. A cleansing product in the form of a napkin comprising the sheet of claim 1.

12. A cleansing product in the form of a product roll comprising the sheet of claim 1.

13. A cleansing product in the form of a wet wipe comprising the sheet of claim 1, the wet wipe being enclosed in a sealed envelope.

14. A cleansing product in the form of a napkin comprising:
   a sheet of nonwoven material, the sheet of nonwoven material comprising:
   fibers arranged at random and a copolymer,
   the copolymer comprising a 4-acryloylamido-phenyl-α-D-mannopyranoside carbohydrate derivative copolymerized with acrylamide;
   the copolymer and fibers being mixed and heat treated to form a sheet of nonwoven material in which the copolymer is carried by the fibers; and the sheet being effective to remove bacteria from a site to be cleaned.

15. The sheet of claim 14, wherein the fibers are cellulose or rayon, and the copolymer further comprises vinylacetate and ethylene.

16. The sheet as in claim 15, wherein the amount of cellulose ranges from substantially 5% to substantially 50% by weight.

17. The sheet of claim 16, wherein the amount of cellulose is about 40% by weight.

18. The sheet of claim 15, wherein the amount of rayon ranges from substantially 5% to substantially 50% by weight.

19. The sheet of claim 18, wherein the amount of rayon is about 40% by weight.

20. The sheet of claim 15, wherein the amount of copolymer ranges from substantially 5% to substantially 40% by weight.

21. The sheet of claim 20, wherein the amount of copolymer is about 20% by weight.

22. The sheet of claim 14, wherein the carbohydrate derivative copolymerized with acrylamide is a D-mannose derivative.

23. A cleansing product in the form of a product roll comprising:
   sheet of nonwoven material, the sheet of nonwoven material comprising:
   fibers arranged at random and a copolymer,
   the copolymer comprising a 4-acryloylamido-phenyl-α-D-mannopyranoside copolymerized with acrylamide carbohydrate derivative;
   the copolymer and fibers being mixed and heat treated to form a sheet of nonwoven material in which the copolymer is carried by the fibers; and the sheet being effective to remove bacteria from a site to be cleaned.

24. The sheet of claim 23, wherein the fibers are cellulose or rayon, and the copolymer further comprises vinylacetate and ethylene.

25. The sheet as in claim 24, wherein the amount of cellulose ranges from substantially 5% to substantially 50% by weight.

26. The sheet of claim 25, wherein the amount of cellulose is about 40% by weight.

27. The sheet of claim 24, wherein the amount of rayon ranges from substantially 5% to substantially 50% by weight.

28. The sheet of claim 27, wherein the amount of rayon is about 40% by weight.

29. The sheet of claim 24, wherein the amount of copolymer ranges from substantially 5% to substantially 40% by weight.

30. The sheet of claim 29, wherein the amount of copolymer is about 20% by weight.

31. The sheet of claim 23, wherein the carbohydrate derivative copolymerized with acrylamide is a D-mannose derivative.

32. A cleansing product in the form of a wet wipe comprising:

a sheet of nonwoven material, the sheet of nonwoven material comprising:
fibers arranged at random and a copolymer, copolymer comprising a 4-acryloylamido-phenyl-α-D-mannopyranoside carbohydrate derivative copolymerized with acrylamide;
the copolymer and fibers being mixed and heat treated to form a sheet of nonwoven material in which the copolymer is carried by the fibers; the sheet being effective to remove bacteria from a site to be cleaned; and the wet wipe being enclosed in a sealed envelope.

33. The sheet of claim 32, wherein the fibers are cellulose or rayon, and the copolymer further comprises vinylacetate and ethylene.

34. The sheet as in claim 33, wherein the amount of cellulose ranges from substantially 5% to substantially 50% by weight.

35. The sheet of claim 34, wherein the amount of cellulose is about 40% by weight.

36. The sheet of claim 33, wherein the amount of rayon ranges from substantially 5% to substantially 50% by weight.

37. The sheet of claim 36, wherein the amount of rayon is about 40% by weight.

38. The sheet of claim 33, wherein the amount of copolymer ranges from substantially 5% to substantially 40% by weight.

39. The sheet of claim 38, wherein the amount of copolymer is about 20% by weight.

40. The sheet of claim 32, wherein the carbohydrate derivative copolymerized with acrylamide is a D-mannose derivative.

41. The sheet of claim 1, wherein the copolymer:
has a molecular weight of about 5 kDa to about 2000 kDa; and
has a formula in which $R^2$ has the formula:

wherein $R^3$ is H or $CH_3$;
x is an integer from 1 to about 20; and
x is an integer varying for each m unit ($[\,]_m$) in the copolymer with an average value of x for a copolymer between 1 and 20.

* * * * *